(12) United States Patent
Watson et al.

(10) Patent No.: US 6,551,628 B1
(45) Date of Patent: Apr. 22, 2003

(54) HERBAL INTESTINAL TRACT CLEANSER

(75) Inventors: Tommy Stanley Watson, Dunedin, FL (US); Brenda F. Watson, Dunedin, FL (US)

(73) Assignee: Renew Life Formulas, Inc., Clearwater, FL (US)

(*) Notice: Subject to any disclaimer, the term of this patent is extended or adjusted under 35 U.S.C. 154(b) by 0 days.

(21) Appl. No.: 09/997,360

(22) Filed: Nov. 30, 2001

(51) Int. Cl.[7] .................................................. A61K 35/78
(52) U.S. Cl. ..................... 424/725; 424/732; 424/736; 424/739; 424/745; 424/747; 424/754; 424/761; 424/773; 424/774; 424/777
(58) Field of Search ............................. 424/725, 195.1, 424/732, 736, 739, 745, 747, 754, 761, 773, 774, 777

(56) References Cited

U.S. PATENT DOCUMENTS

| | | | | |
|---|---|---|---|---|
| 4,851,252 A | * | 7/1989 | Greither et al. ............. | 426/599 |
| 5,885,600 A | * | 3/1999 | Blum et al. .................. | 424/405 |

* cited by examiner

*Primary Examiner*—Christopher R. Tate
*Assistant Examiner*—Patricia Patten
(74) *Attorney, Agent, or Firm*—Donald R. Fraser

(57) ABSTRACT

An herbal formulation comprises a liquid component and a solid component. The liquid component comprises oregano leaf, orange peel, Oregon grape root, pau d' arco, cinnamon bark, clove bud, and peppermint leaf. The solid component comprises uva ursi, garlic bulb, magnesium caprylate, citricidal extract, pau d' arco, calcium undecylenate, barberry root, neem leaf, olive leaf, and berberine sulphate.

20 Claims, No Drawings

HERBAL INTESTINAL TRACT CLEANSER

FIELD OF THE INVENTION

This invention relates generally to an herbal food supplement and intestinal tract cleanser. More particularly, the invention is directed to an herbal formulation useful for cleansing Candida from the intestinal tract of the human body.

BACKGROUND OF THE INVENTION

Herbal formulations can provide a supplement to the daily human diet, and additionally can provide a natural way to cleanse the intestinal tract of Candida, as well as other toxins and food particles. Such formulations are useful for treating a condition known as "leaky gut."

Leaky gut is a condition in which the mucosa of the intestinal tract is compromised, thereby allowing toxins and food particles to penetrate the lining of the intestinal tract and enter the body's blood stream. The body itself may naturally attempt to counteract this phenomenon, usually with several negative side effects. Firstly, the body may attempt to produce antibodies to combat the toxins. This will result in the body developing allergies to the foods which have caused the breakdown of the intestinal tract lining. Furthermore, the liver may increase its production of detoxifying enzymes. The activation of some of these enzymes may release harmful free radicals as a byproduct. These oxidizing free radicals may, in turn, damage the liver and other tissues, resulting in a weakened immune system. Symptoms of leaky gut may include irritable bowel disease, chronic fatigue, food allergies, and arthritis.

*Candida Albicans,* a common yeast, is part of the regular flora (bacteria) in the digestive tract. In a healthy state, the Candida exist in a ratio of about one Candida per one million other bacteria. Due to many modern-day factors, this yeast can proliferate beyond correct proportion. Yeast overgrowth related disorders may then develop, such as yeast infections, rectal itch, constipation, bloating, skin problems, and the like.

With long term infestation, Candida yeast shifts to a fungal form, developing roots called rhizoids that can grow into the intestinal wall. These rhizoids cause the intestine to become porous (leaky gut), allowing toxins and undigested proteins and carbohydrates to flow through the bowel wall and be absorbed into the body and blood stream. The immune system then produces antibodies (proteins) which attempt to neutralize the Candida overgrowth. These antibodies can cause the body to become hypersensitive to certain foods and molds, create a variety of food allergies, interfere with hormonal activity, and cause nutritional deficiencies.

It would be desirable to prepare an herbal formulation which would act as a food supplement as well as cleanse Candida from the body's intestinal tract, thus allowing rejuvenation of the intestinal tract lining to diminish the passage there through of toxins and food particles.

SUMMARY OF THE INVENTION

Accordant with the present invention, there surprisingly has been discovered an herbal formulation which acts as a food supplement, and is useful for cleansing Candida from the intestinal tract. The herbal formulation comprises a liquid and a solid, said liquid comprising:

oregano leaf;
orange peel;
Oregon grape root;
pau d' arco;
cinnamon bark;
clove bud; and
peppermint leaf; and said solid comprising:

uva ursi;
garlic bulb;
magnesium caprylate;
citricidal extract;
pau d' arco;
calcium undecylenate;
barberry root;
neem leaf;
olive leaf; and
berberine sulphate.

The herbal formulation of the present invention is useful as a food supplement, and is additionally particularly useful for cleansing Candida from the body's intestinal tract.

DETAILED DESCRIPTION OF THE PREFERRED EMBODIMENTS

The present invention is directed to an herbal formulation useful as a food supplement and for cleansing Candida from the body's intestinal tract. The formulation comprises a liquid and a solid. The liquid comprises: oregano leaf; orange peel; Oregon grape root; pau d' arco; cinnamon bark; clove bud; and peppermint leaf. The solid comprises: uva ursi; garlic bulb; magnesium caprylate; citricidal extract; pau d' arco; calcium undecylenate; barberry root; neem leaf; olive leaf; and berberine sulphate. All of the recited ingredients are well-known in the food supplements and nutrition industry.

The liquid component of the herbal formulation is typically dispensed from a dropper bottle, so that the liquid may be placed drop-wise into a drink. The solid component may be compressed and formed into a tablet, which can then be swallowed. The herbal formulation according to the present invention is designed to be taken orally.

Pau d' arco is present in both the liquid and solid components of the inventive formulation, acting as an antibacterial agent. The pau d' arco may comprise from about 10 to about 20 weight percent of the liquid component of the formulation, and from about 5 to about 15 weight percent of the solid component of the formulation. Preferably, the pau d', arco comprises about 16 weight percent of the liquid component, and about 8 weight percent of the solid component.

Oregano leaf is present in the liquid component, and acts as an antifungal and antimicrobial agent. The oregano leaf may comprise from about 10 to about 30 weight percent of the liquid component. Preferably, the oregano leaf comprises about 20 weight percent of the liquid component.

Orange peel is present in the liquid component, acting as a digestive aid. The orange peel may comprise from about 15 to about 25 weight percent of the liquid component. Preferably, the orange peel comprises about 16 weight percent of the liquid component.

Oregon grape root is present in the liquid component, and acts as an antioxidant and antifungal agent. The Oregon grape root may comprise from about 10 to about 20 weight percent of the liquid component. Preferably, the Oregon grape root comprises about 16 weight percent of the liquid component.

Cinnamon bark is present in the liquid component, acting as a digestive aid. The cinnamon bark may comprise from about 5 to about 15 weight percent of the liquid component. Preferably, the cinnamon bark comprises about 10 weight percent of the liquid component.

Clove bud is present in the liquid component, and acts as a digestive aid and flatulent. The clove bud may comprise from about 5 to about 15 weight percent of the liquid component. Preferably, the clove bud comprises about 10 weight percent of the liquid component.

Peppermint leaf is present in the liquid component, acting as an anti-spasmodic agent. The peppermint leaf may comprise from about 5 to about 15 weight percent of the liquid component. Preferably, the peppermint leaf comprises about 10 weight percent of the liquid component. Uva ursi is present in the solid component, and acts as an astringent and diuretic. The uva ursi may comprise from about 20 to about 40 weight percent of the solid component. Preferably, the uva ursi comprises about 32 weight percent of the solid component.

Garlic bulb is present in the solid component, acting as an antifungal and antibacterial agent. The garlic bulb may comprise from about 10 to about 20 weight percent of the solid component. Preferably, the garlic bulb comprises about 16 weight percent of the solid component.

Magnesium caprylate is present in the solid component, and acts as a fungicidal agent. The magnesium caprylate may comprise from about 5 to about 15 weight percent of the solid component. Preferably, the magnesium caprylate comprises about 8 weight percent of the solid component.

Citricidal extract, made of grapefruit seed and rind, is present in the solid component, acting as an antifungal agent. The citricidal extract may comprise from about 5 to about 15 weight percent of the solid component. Preferably, the citricidal extract comprises about 8 weight percent of the solid component.

Calcium undecylenate is present in the solid component, and acts as an antifungal agent. The calcium undecylenate may comprise from about 5 to about 15 weight percent of the solid component. Preferably, the calcium undecylenate comprises about 8 weight percent of the solid component.

Barberry root is present in the solid component, acting as a hepatic aid and laxative. The barberry root may comprise from about 2 to about 10 weight percent of the solid component. Preferably, the barberry root comprises about 5 weight percent of the solid component.

Neem leaf is present in the solid component, and acts as an antibacterial and antifungal agent. The neem leaf may comprise from about 2 to about 10 weight percent of the solid component. Preferably, the neem leaf comprises about 5 weight percent of the solid component.

Olive leaf is present in the solid component, acting as an antimicrobial agent. The olive leaf may comprise from about 2 to about 10 weight percent of the solid component. Preferably, the olive leaf comprises about 5 weight percent of the sold component.

Berberine sulphate is present in the solid component, and acts as an anti-inflammatory and antimicrobial agent. The berberine sulphate may comprise from about 1 to about 5 weight percent of the solid component. Preferably, the berberine sulphate comprises about 3 weight percent of the solid component.

The ingredients that comprise the solid component of the inventive formulation may be ground individually by conventional methods, and compressed with an inert carrier to form tablets for oral administration. The ingredients that comprise the liquid component may be ground individually and placed in a suspension of, for example, an approximately equal amount by weight of water and ethyl alcohol.

The effective daily dosage for the food supplement and herbal intestinal tract cleaner according to the present invention ranges from about 100 mg per day to about 1,000 mg per day for the liquid component, and from about 300 mg per day to about 2,500 mg per day for the solid component. Preferably, the effective dosage is about 400 mg per day for the liquid component and about 925 mg per day for the solid component. The food supplement and herbal intestinal tract cleaner according to the present invention is taken orally.

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. An herbal formulation, comprising a liquid and a solid, said liquid comprising:
   oregano leaf;
   orange peel;
   Oregon grape root;
   pau d' arco;
   cinnamon bark;
   clove bud; and
   peppermint leaf; and
said solid comprising:
   uva ursi;
   garlic bulb;
   magnesium caprylate;
   citricidal extract;
   pau d' arco;
   calcium undecylenate;
   barberry root;
   neem leaf;
   olive leaf; and
   berberine sulphate.

2. The herbal formulation according to claim 1, wherein the concentration of oregano leaf ranges from about 10 to about 30 weight percent of the liquid component.

3. The herbal formulation according to claim 1, wherein the concentration of orange peel ranges from about 10 to about 20 weight percent of the liquid component.

4. The herbal formulation according to claim 1, wherein the concentration of Oregon grape root ranges from about 10 to about 20 weight percent of the liquid component.

5. The herbal formulation according to claim 1, wherein the concentration of pau d' arco ranges from about 10 to about 20 weight percent of the liquid component.

6. The herbal formulation according to claim 1, wherein the concentration of cinnamon bark ranges from about 5 to about 15 weight percent of the liquid component.

7. The herbal formulation according to claim 1, wherein the concentration of clove bud ranges from about 5 to about 15 weight percent of the liquid component.

8. The herbal formulation according to claim 1, wherein the concentration of peppermint leaf ranges from about 5 to about 15 weight percent of the liquid component.

9. The herbal formulation according to claim 1, wherein the concentration of uva ursi ranges from about 20 to about 40 weight percent of the solid component.

10. The herbal formulation according to claim 1, wherein the concentration of garlic bulb ranges from about 10 to about 20 weight percent of the solid component.

11. The herbal formulation according to claim 1, wherein the concentration of magnesium caprylate ranges from about 5 to about 15 weight percent of the solid component.

12. The herbal formulation according to claim 1, wherein the concentration of citricidal extract ranges from about 5 to about 15 weight percent of the solid component.

13. The herbal formulation according to claim 1, wherein the concentration of pau d' arco ranges from about 5 to about 15 weight percent of the solid component.

14. The herbal formulation according to claim 1, wherein the concentration of calcium undecylenate ranges from about 5 to about 15 weight percent of the solid component.

15. The herbal formulation according to claim 1, wherein the concentration of barberry root ranges from about 2 to about 10 weight percent of the solid component.

16. The herbal formulation according to claim 1, wherein the concentration of neem leaf ranges from about 2 to about 10 weight percent of the solid component.

17. The herbal formulation according to claim 1, wherein the concentration of olive leaf ranges from about 2 to about 10 weight percent of the solid component.

18. The herbal formulation according to claim 1, wherein the concentration of berberine sulphate ranges from about 1 to about 5 weight percent of the solid component.

19. An herbal formulation, comprising a liquid and a solid, said liquid comprising:

from about 10 to about 30 weight percent oregano leaf;

from about 10 to about 20 weight percent orange peel;

from about 10 to about 20 weight percent Oregon grape root;

from about 10 to about 20 weight percent pau d' arco;

from about 5 to about 15 weight percent cinnamon bark;

from about 5 to about 15 weight percent clove bud; and from about 5 to about 15 weight percent peppermint leaf; and said solid comprising:

from about 20 to about 40 weight percent uva ursi;

from about 10 to about 20 weight percent garlic bulb;

from about 5 to about 15 weight percent magnesium caprylate;

from about 5 to about 15 weight percent citricidal extract;

from about 5 to about 15 weight percent pau d' arco;

from about 5 to about 15 weight percent calcium undecylenate;

from about 2 to about 10 weight percent barberry root;

from about 2 to about 10 weight percent neem leaf;

from about 2 to about 10 weight percent olive leaf; and from about 1 to about 5 weight percent berberine sulphate.

20. An herbal formulation, comprising a liquid and a solid, said liquid comprising:

about 20 weight percent oregano leaf;

about 16 weight percent orange peel;

about 16 weight percent Oregon grape root;

about 16 weight percent pau d' arco;

about 10 weight percent cinnamon bark;

about 10 weight percent clove bud; and about 10 weight percent peppermint leaf; and said solid comprising:

about 32 weight percent uva ursi;

about 16 weight percent garlic bulb;

about 8 weight percent magnesium caprylate;

about 8 weight percent citricidal extract;

about 8 weight percent pau d' arco;

about 8 weight percent calcium undecylenate;

about 5 weight percent barberry root;

about 5 weight percent neem leaf;

about 5 weight percent olive leaf; and about 3 weight percent berberine sulphate.

* * * * *